United States Patent [19]

Levy

[11] Patent Number: 5,194,005
[45] Date of Patent: Mar. 16, 1993

[54] SURGICAL AND DENTAL PROCEDURES USING LASER RADIATION

[75] Inventor: Guy Levy, Marseille, France

[73] Assignee: Laser Medical Technology, Inc., San Clemente, Calif.

[21] Appl. No.: 351,203

[22] Filed: May 15, 1989

Related U.S. Application Data

[63] Continuation-in-part of Ser. No. 299,472, Jan. 18, 1989, Pat. No. 5,020,995, and Ser. No. 335,245, Apr. 10, 1989, abandoned.

[30] Foreign Application Priority Data

Dec. 21, 1988 [FR] France ............................ 88 17549

[51] Int. Cl.$^5$ ............................................. A61C 3/00
[52] U.S. Cl. ..................................... 433/215; 433/224; 606/10
[58] Field of Search ............... 433/215, 216, 226, 224, 433/29; 606/3, 10, 15, 16, 2; 128/395, 398

[56] References Cited

U.S. PATENT DOCUMENTS

| | | | |
|---|---|---|---|
| 3,821,510 | 6/1974 | Muncheryan | 128/395 |
| 3,858,577 | 1/1975 | Bass et al. | 128/8 |
| 4,045,119 | 8/1977 | Eastgate | 350/96 LM |
| 4,152,575 | 5/1979 | Banas | 219/121 LM |
| 4,170,997 | 10/1979 | Pinnow et al. | 128/395 |
| 4,273,535 | 6/1981 | Yamamoto | 433/216 |
| 4,503,853 | 3/1985 | Ota et al. | 606/16 |
| 4,521,194 | 6/1985 | Meyers et al. | 606/10 |
| 4,538,609 | 9/1985 | Takenaka et al. | 606/16 |
| 4,736,745 | 4/1988 | Gluckman | 128/303.1 |
| 4,784,135 | 11/1988 | Blum et al. | 606/3 |
| 4,940,411 | 7/1990 | Vassiliadis et al. | 606/16 |

OTHER PUBLICATIONS

"Removal of Oral Soft Tissue Pathology With The $CO_2$ Laser"; by J. W. Frame; J. Oral Maxillofac. Surg. 43:850–855, 1985.

"Carbon Dioxide Laser Surgery for Bening Oral Lesions"; by J. W. Frame; British Dental Journal 1985; 158:125.

Nelson et al, "Ablation of Bone & Methacrylate by a Prototype Mid-Infrared Erbium:YAG Laser", *Lasers in Surgery and Medicine*, 8:494–500 (1988), pp. 494–500.

*Primary Examiner*—Cary E. O'Connor
*Attorney, Agent, or Firm*—Spensley Horn Jubas & Lubitz

[57] ABSTRACT

Laser radiation having a selected wavelength and in the form of pulses having a selected pulse duration, repetition rate and energy content per pulse, is employed for performing a variety of dental and medical procedures, including treatment of cysts and granulomas in the gum, and cutting of dentin, cementum, dental root material, bone and metal. Cavities and openings in teeth and bones can be filled with a mixture containing hydroxyapatite and phosphoric acid, mixed together to form a paste, and the resulting mixture, after being introduced into the openign or cavity, can be cured and hardened by application of pulses of defocussed laser radiation.

16 Claims, No Drawings

SURGICAL AND DENTAL PROCEDURES USING LASER RADIATION

CROSS REFERENCE TO RELATED APPLICATION

This is a continuation-in-part of application Ser. No. 07/299,472, filed on Jan. 18, 1989, now U.S. Pat. No. 5,020,995, and application Ser. No. 07/335,245, filed on Apr. 10, 1989, now abandoned.

BACKGROUND OF THE INVENTION

The present invention relates to surgical and dental procedures utilizing laser radiation.

In the treatment of various dental and other medical conditions, it is frequently necessary to remove bone, dentin, cementum or dental root material, and it is desirable to do so without subjecting the patient to adverse side effects.

Frequently, when performing medical procedures within the oral cavity, the practitioner encounters metal bodies introduced by previous dental procedures, such bodies being constituted by metal filling material, metal pins, and chrome posts used to secure dental prostheses in place, and it is necessary to cut these bodies, again without producing harmful side effects.

Also, dental practitioners frequently encounter cysts and granulomas, which occur in the gum adjacent the apex of a tooth, and it is necessary to destroy, or at least substantially reduce, these growths.

Furthermore, while a number of dental filling materials are presently available, there is a continuing need for material which can fill not only dental cavities, but also cavities existing in, or created in, bone material, and which will have a hardness comparable to that of the natural material which it replaces and form a strong bond with the wall of the cavity or opening.

SUMMARY OF THE INVENTION

It is an object of the present invention to effectively employ laser radiation to perform the procedures described above in an improved manner.

A more specific object of the invention is to employ laser radiation for selectively cutting bone, dentin, cementum and dental root material, as well as metal bodies found in the mouth, without exposing the patient to adverse side effects, and particularly burning of tissue adjacent the area being treated.

Another object of the invention is to provide a novel filling material for filling cavities or openings in both teeth and bones, and to employ laser radiation for promoting hardening of such filling material.

Yet another object of the invention is to provide an improved treatment for cysts and granulomas in bones and in the gum.

According to one aspect of the invention, the above objects are achieved by a method for filling an opening in tooth or bone material comprising:
 forming a paste composed of a liquid and a powder containing hydroxyapatite;
 filling the opening with the paste; and
 irradiating the paste which fills the opening with laser radiation in order to bond the hydroxyapatite to material surrounding the opening.

According to another aspect of the invention, the objects are achieved by a method of treating a cyst or granuloma in the gum at the apex of a tooth canal, or in bone, comprising:
 opening the canal to the vicinity of the apex;
 inserting an optical fiber having an output end into the canal so that the output end is located at the apex; and
 conducting a succession of pulses of radiation through the fiber so that the radiation exits from the output end, impinges on and opens the foramen, and then impinges on and at least reduces the cyst or granuloma.

According to yet another aspect of the invention, the objects are achieved by a method for cutting bone, dentin, cementum and dental root material in the body, comprising: generating laser radiation having a wavelength suitable for cutting such material; producing successive pulses of the radiation with an energy level, pulse duration and repetition rate selected to cut the material without causing harmful side effects; concentrating the radiation pulses on the material to a spot sufficiently small to cause cutting of the material; and, simultaneously with the step of concentrating, directing a cooling fluid onto the spot.

According to still another aspect of the invention, the objects are achieved by a method for cutting metal bodies in the mouth of a patient, comprising: generating laser radiation having a wavelength suitable for cutting the metal; producing successive pulses of the radiation with an energy level, pulse duration and repetition rate selected to cut the metal without causing harmful side effects; concentrating the radiation pulses on the metal to a spot sufficiently small to cause cutting of the metal; and, simultaneously with the step of concentrating, directing a cooling fluid onto the spot.

DESCRIPTION OF THE PREFERRED EMBODIMENTS

The application of laser radiation in all of the procedures to be described herein can be carried out with the apparatus described and illustrated in copending U.S. application Ser. No. 07/299,472, filed Jan. 18, 1989, the entirety of which is here incorporated by reference.

According to a first aspect of the invention, a filling material for teeth is constituted by a mixture formed from a liquid component composed of phosphoric acid and water and a powder component composed of a ceramic and hydroxyapatite, with the ingredients mixed in a proportion to form a paste having a consistency such that the paste is workable and sufficiently self-supporting to be applied to the opening with a spatula and remain in place, and laser radiation having the characteristics to be described below is applied to cure and harden the mixture and bond it to the tooth. The proportions of the mixture are not critical, however, the following are preferred:

| Liquid: | Phosphoric acid | 40% |
|---------|-----------------|-----|
|         | Water           | 60% |
| Powder: | Ceramic         | 80% |
|         | Hydroxyapatite  | 20% |

If the proportion of hydroxyapatite is increased, more energy is required to harden the mixture; if it is decreased, the strength of the resulting bond is reduced.

The ceramic component may be composed of corderite, silica or silicium oxide, or aluminum oxide, for example. The powder components will have the grain sizes normally used for dental filling materials.

The liquid and powder components should be mixed together just prior to introduction into the opening to be filled.

The radiation applied during this treatment has a wavelength of 1.06μ and is composed of pulses preferably having a duration of the order of 0.4 ms, a repetition rate of the order of 50 Hz and an energy per pulse in the range of 20–100 mJ. However, in contrast to the various cutting operations to be described in detail below, the beam should here be defocussed to be at least approximately coextensive with the exposed surface of the filling material. This can easily be achieved by varying the spacing between the radiation output surface of the handpiece and the tooth surface, the area of illumination being readily visible.

The application of radiation to the filling material will promote the growth of a crystal structure in that material and create a strong bond between the hydroxy-apatite and the surrounding tooth material.

The radiation will be applied until a crystal structure appears, this generally requiring application of the radiation for a period of 10–30 seconds.

The above described filling material and radiation can be used for filling breaks or gaps in bone material.

According to another aspect of the invention, radiation having the above-described characteristics can be employed for treating a cyst or granuloma adjacent a tooth apex, or in bone. For this purpose, after the canal had been opened to the foramen, a narrow optical fiber, having a diameter of around 200μ, for example, is threaded into the canal up to the foramen, and radiation having the characteristics described above for cutting soft tissue is delivered through the fiber to cut the foramen and then eliminate the cyst or granuloma. The procedure employed for opening the canal to the foramen can be performed in the manner described in the above-cited U.S. application Ser. No. 299,472 or in the manner described below in connection with cutting, inter alia, root material and dentin.

For this operation, use is preferably made of radiation having a wavelength of 1.06μ, a pulse duration of the order of 0.4 ms, a pulse repetition rate of the order of 50 Hz and an energy content per pulse of 50–400 mJ.

In further accordance with the invention, it is possible to cut, without burning, bone, root, dentin and cementum in periods of the order of seconds by applying radiation of the type described above together with irrigation with a water/air mixture to control the thermal laser beam cutting action. In this case, the radiation wavelength is 1.06μ, the pulse duration is of the order of 0.8–1.2 ms, the pulse repetition rate is in the range of 30–50 Hz and the energy content per pulse is 200–400 mJ. This can be done without first forming a dark spot where the radiation is first applied. However, application of a dark spot will increase energy absorption and thus speed the cutting operation. In addition, a dark spot can be applied when it is desired to preliminarily mark or outline with a low energy beam the place to be cut.

In addition, radiation having the form described above for cutting bone can further serve to cut metal parts in the mouth, such as metal fillings, pins, or chrome tooth prosthesis posts. For this purpose laser radiation will be created and directed to the material to be cut in the manner described above.

In the performance of all of the cutting operations described above, the light output surface of the handpiece is positioned to focus the radiation to a small spot, preferably having a diameter of the order of 200–600μ.

When dentin is cut with the aid of an optical fiber in contact with the dentin, the end of the fiber in contact with the dentin is subject to destruction. Therefore, it is desirable to use a relatively long fiber which will be replaced after a period of use.

While the description above refers to particular embodiments of the present invention, it will be understood that many modifications may be made without departing from the spirit thereof. The accompanying claims are intended to cover such modifications as would fall within the true scope and spirit of the present invention.

The presently disclosed embodiments are therefore to be considered in all respects as illustrative and not restrictive, the scope of the invention being indicated by the appended claims, rather than the foregoing description, and all changes which come within the meaning and range of equivalency of the claims are therefore intended to be embraced therein.

What is claimed is:

1. A method of treating a cyst or adjacent the apex of a tooth canal, comprising:
   opening the canal to the vicinity of the apex;
   inserting an optical fiber having an output end into the canal so that the output end is located at the apex; and
   conducting a succession of pulses of radiation through the fiber so that the radiation exits from the output end, impinges on and opens the foramen, and then impinges on and at least reduces the cyst or granuloma.

2. A method as defined in claim 1 wherein the radiation has a wavelength of the order of 1.06μ.

3. A method as defined in claim 2 wherein the radiation is composed of pulses having a duration of the order of 0.4 ms, and a repetition rate of the order of 50 Hz.

4. A method as defined in claim 3 wherein the radiation has an energy content in the range of 50–400 mJ per pulse.

5. A method for treating a cyst or granuloma adjacent the apex of a tooth, the tooth having a canal which extends to a foramen at the apex, comprising: generating laser radiation having a wavelength suitable for cutting material in the tooth canal; producing successive pulses of the radiation with an energy level, pulse duration and repetition rate selected to cut the material in the tooth canal without causing harmful side effects; concentrating the radiation pulses on the material to a spot sufficiently small to cause cutting of the material; simultaneously with said step of concentrating, directing a cooling fluid onto the spot;
   inserting an optical fiber having an output end into the canal so that the output end of the fiber is located at the tooth apex; and
   conducting a succession of pulses of radiation through the fiber so that the radiation exits from the output end of the fiber, impinges on and opens the foramen, and then impinges on and at least reduces the cyst or granuloma.

6. A method as defined in claim 5 wherein the radiation has a wavelength of the order of 1.06μ.

7. A method as defined in claim 6 wherein during said step of producing the radiation is composed of pulses having a duration of the order of 0.8–1.2 ms, and a repetition rate in the range of 30–50 Hz.

8. A method as defined in claim 7 wherein during said step of producing the radiation has an energy content of the order of 200–400 mJ per pulse.

9. A method as defined in claim 6 wherein during said step of conducting the radiation is composed of pulses having a duration of the order of 0.4 ms, and a repetition rate of the order of 50 Hz.

10. A method as defined in claim 9 wherein during said step of conducting the radiation has an energy content in the range of 50–400 mJ per pulse.

11. A method as defined in claim 5 wherein the cooling fluid is a mixture of air and water.

12. A method for cutting bone in the body, comprising: generating laser radiation having a wavelength suitable for cutting bone; producing successive pulses of the radiation with an energy level, pulse duration and repetition rate selected to cut the bone without causing harmful side effects; concentrating the radiation pulses on the bone to a spot sufficiently small to cause cutting of the bone; and, simultaneously with said step of concentrating, directing a cooling fluid containing water onto the spot.

13. A method as defined in claim 12 wherein the radiation has a wavelength of the order of $1.06\mu$.

14. A method as defined in claim 13 wherein the radiation is composed of pulses having a duration of the order of 0.8–1.2 ms, and a repetition rate in the range of 30–50 Hz.

15. A method as defined in claim 14 wherein the radiation has an energy content of the order of 200–400 mJ per pulse.

16. A method as defined in claim 12 wherein the cooling fluid is a mixture of air and water.

* * * * *